United States Patent
Averill et al.

[11] Patent Number: 5,863,295
[45] Date of Patent: Jan. 26, 1999

[54] PROSTHETIC DEVICE AND METHOD OF IMPLANTATION

[75] Inventors: Robert G. Averill, Ringwood; Robert C. Cohen, Rockaway Township; Rafail Zubok, Midland Park, all of N.J.

[73] Assignee: Implex Corporation, Alendale, N.J.

[21] Appl. No.: 844,443

[22] Filed: Apr. 18, 1997

Related U.S. Application Data

[62] Division of Ser. No. 636,727, Apr. 23, 1996, Pat. No. 5,702,487, which is a continuation of Ser. No. 252,450, Jun. 1, 1994, abandoned.

[51] Int. Cl.⁶ .................................................. A61F 2/36
[52] U.S. Cl. ............................................................ 623/23
[58] Field of Search .................... 606/80, 85; 623/22, 623/23

[56] References Cited

U.S. PATENT DOCUMENTS

| | | |
|---|---|---|
| 4,064,567 | 12/1977 | Burstein et al. . |
| 4,514,865 | 5/1985 | Harris . |
| 4,530,116 | 7/1985 | Frey . |
| 4,549,319 | 10/1985 | Meyer . |
| 4,608,053 | 8/1986 | Keller . |
| 4,718,915 | 1/1988 | Epinette . |
| 4,955,912 | 9/1990 | Berchem . |
| 5,007,931 | 4/1991 | Smith . |
| 5,018,285 | 5/1991 | Zolman et al. . |
| 5,035,717 | 7/1991 | Brooks . |
| 5,061,287 | 10/1991 | Feiler . |
| 5,092,899 | 3/1992 | Forte . |
| 5,092,900 | 3/1992 | Marchetti et al. . |
| 5,108,405 | 4/1992 | Mikhail et al. ............................ 606/80 |
| 5,108,437 | 4/1992 | Kenna . |
| 5,147,408 | 9/1992 | Noble et al. .............................. 606/85 |
| 5,169,401 | 12/1992 | Lester et al. .............................. 606/80 |
| 5,171,275 | 12/1992 | Ling et al. . |
| 5,342,363 | 8/1994 | Richelsoph ............................... 606/80 |

*Primary Examiner*—Debra S. Brittingham
*Attorney, Agent, or Firm*—Plevy & Associates

[57] ABSTRACT

A hip prosthesis for implanting into the medullary canal of a femur, which comprises a stem for implanting into the canal of the femur, the stem having a proximal end and a distal end, the stem also including a proximal locking zone substantially adjacent the proximal end, the proximal locking zone including a proximal locking surface which circumferentially press-fits within the canal of the femur and a neck extending at an angle from the proximal end of the stem for receiving the femoral head of the prosthesis.

6 Claims, 9 Drawing Sheets

PROSTHETIC DEVICE AND METHOD OF IMPLANTATION

This is a Divisional of application Ser. No. 08/636,727, filed on Apr. 23, 1996 for PROSTHETIC DEVICE AND METHOD OF IMPLANTATION now U.S. Pat. No. 5,702,487, which is a continuation of Ser. No. 08/252,450, filed Jun. 1, 1994 for PROSTHETIC DEVICE AND METHOD OF IMPLANTATION, now abandoned.

FIELD OF THE INVENTION

The present invention relates generally to a prosthetic device and in particular, to a prosthetic bone implant which is implanted into a proximal femur in a press-fit manner.

BACKGROUND OF THE INVENTION

Prosthetic devices are utilized for replacing load-carrying skeletal members, such as the human hip, which are rendered non-functional due to acute arthritis, fracture, resections for malignancy or malformation. Such procedures have become more commonplace not only in human beings but also in animals such as dogs.

Hip joints are commonly repaired by total joint replacement with artificial components. Such hip prostheses typically include a femoral portion or component which is implanted in the femur and an acetabular component which is secured to the pelvis. The femoral component includes a head which articulates in a socket formed in the acetabular component.

With prostheses, especially a hip prosthesis, it is desirable to provide a rigid fixation of the prosthesis in order to provide long term stabilization, to minimize bone-implant micromotion, and to minimize the occurrence of complications, such as pain, after surgery.

Many known prosthetic devices require rigid fixation through the use of cement for the embedment of the prosthesis into the bone structure. These types of devices, however, display a number of disadvantages; during the installation of the prosthesis, it is typically necessary to wait, after sealing the shaft, until the cement has acquired sufficient resistance by polymerization before proceeding. During setting of the cement, the cement releases heat and can cause damage to surrounding tissue. The presence of the cement also inhibits the ingrowth of bone into the prothesis.

Another problem associated with prior art cemented prostheses is that they are designed to be firmly attached along their entire length. In the case of a hip prosthesis, the entire length of the stem of the femoral component is either cemented to the intramedullary canal of the femur to insure adequate stability. This causes compressive and other stresses created in and through the stem, when the leg is used, to be transferred to the femoral bone near the distal end of the prosthetic stem not uniformly along its length. The fixation created between the cement and the portion of the bone surrounding the lower portion of the stem transfers the forces developed through the ball joint to the lower portion of the femur and bypasses its proximal end. Over time, that portion of the femur is subject to deterioration of osteoporosis and thinning of the bone. As a result, the proximal end of the femur essentially loses density causing eventual loosening of the stem of the prosthesis within the bone. The problems associated with cemented implants have resulted in the development of implants which are inserted into the bone canals to obtain a press-fit arrangement.

In prostheses which are designed to be press-fitted, particularly in the case of press-fit hip femoral stems, two issues affect the clinical performance of the implant. These issues are initial implant stability and bone reactions. A stem design should focus on the tightest fit to resist subsidence and torsional forces and micromotion. The bone should be loaded most proximally in press-fit applications when good bone quality is encountered to stimulate appropriate bone remodeling, for continued implant support, and reduced stress-shielding of that critical region.

The present invention provides an improved geometry of the stem in the proximal bone region by a modification involving the shape of the implant and its interaction with the preparation instruments.

In prior art press-fit implants, an interference fit is provided by a slightly undersized preparation where the anterior and posterior faces of the proximal implant do not compress much bone relative to the medial and lateral portions. The anterior and posterior faces on many of the prior art implants are parallel sided providing no resistance to subsidence. Torsionally, the resistance can be minimal due to the lack of bone quality and contact. With a slightly tapered anterior and posterior face, the bone is slightly compressed in an interference fit. The angle defined by the tapered faces of typical prior art implants is approximately 3 degrees. Due to this slight angle, a linear distance corresponding to the implantation axis provides little outward displacement. Hence, the bone is not compressed to any great extent, which in turn, may contribute to less than optimal initial stability. In addition, the slight angle is not optimal in transferring compressive loads to the bone with most of the initial loads going to the medial proximal portions. Increased anterior/posterior loading occurs only when bone ingrowth occurs and bony remodeling occurs over a broad, mostly medial area. The present invention includes a geometry in the proximal region about the stem which provides a greater angle on the anterior and posterior faces of the stem. The angle on the anterior/posterior sides is at least double that of the prior art tapered stems and is located in a more proximal location.

The improved proximal locking zone of the present invention initially loads the bone more proximally and compresses the bone (in an interference fit) to a greater extent than prior art stems. This provides for densification of bone about the stem, greater resistance to subsidence, and greater resistance to torsional forces. In addition, the densification of bone potentially inhibits the transfer mechanism for implant debris to the boundary surrounding the implant/bone interface. A reduction in the incidence of lysis is also a potential benefit.

To aid in retaining the stem of the present invention, a bio-active material or the like, may be applied to the surfaces in the proximal locking zone. This material and such allow for bony ingrowth into the material which enhances the fixation of the prosthesis within the femur.

It is, therefore, an object of the present invention to provide a prosthesis which will transfer the forces generated in the upper portion of the stem to the proximal portion of the femur through an effective angle and thereby eliminate deterioration of the bone in that area.

It is a further object of the invention to provide a novel method of implanting a femoral stem which prepares the intramedullary canal for the novel geometry of the present invention.

SUMMARY OF THE INVENTION

According to the invention, a hip prosthesis for implanting into the medullary canal of a femur comprises a stem for implanting into the canal of the femur, the stem having a proximal end and a distal end, the stem also including a proximal locking zone substantially adjacent the proximal end, the proximal locking zone including a proximal locking surface which circumferentially press-fits within the canal of the femur and a neck extending at an angle from the proximal end of the stem for receiving the femoral head of the prosthesis.

The stem further defines a longitudinal axis. The proximal locking surface and the longitudinal axis define a proximal locking angle therebetween. This proximal locking angle on the anterior and posterior portions of the proximal locking surface, can range anywhere between 5 and 10 degrees, however, 7 degrees is preferred.

The proximal locking surface extends circumferentially about said stem and can comprise a layer of material which promotes growth of natural bone tissue into the layer of material for enhancing the attachment of the prosthesis to the femur. This layer can comprise a synthetic bone material such as hydroxyapatite or in another embodiment of the invention, a layer comprising a plurality of beads coating the proximal locking surface.

Also according to the invention, a method for implanting a prosthesis stem into a medullary canal of a femur, the prosthesis having a proximal locking zone which presents a geometric profile for press-fit engagement within the canal, the method comprising the steps of resecting a portion of the bone using a template as a guide, reaming a bore along the medullary canal of the bone, inserting a trial implant into the bore to prepare the bore for the geometric profile of the proximal locking zone of the stem removing the trial implant from the bore, and inserting the prosthesis into the bore, the proximal locking zone of the prosthesis engaging the bore in a press-fit engagement to securely lock the prosthesis into the bore for in the medullary canal of the bone.

The step of reaming includes a first reaming with a first cylindrical reamer of a given diameter and a second reaming with a tapered reamer after the first reaming, to prepare the bore for the geometric profile of the prosthesis stem. The step of reaming can also include a second reaming with a second cylindrical reamer having a diameter substantially greater than the diameter of the first cylindrical reamer.

The trial implant includes a proximal locking zone which presents a geometric profile substantially like the geometric profile of the locking zone of the stem, the geometric profile of the trial implant being of a size which is slightly less than a size of the geometric profile of the stem to prepare the bone for the interference fit.

BRIEF DESCRIPTION OF THE DRAWINGS

Reference is now made to the accompanying figures in which.

DETAILED DESCRIPTION OF THE DRAWINGS

In the description which follows, it should be understood that any reference to either orientation or direction is intended only for the purpose of illustration and is not in any way intended to be a limitation of the scope of the present invention.

As used herein, the term "proximal" references to the portion of the prothesis positioned closest to the heart. and the term "distal" refers to the portion of the prothesis positioned farthest from the heart. Also used herein, are the terms "anterior", which references the portion of the prosthesis facing toward the front of the body, and the term "posterior", which references the portion of the prosthesis facing toward the rear of the body. It should be understood, however, that because the device may be used in either the right or left femur, the "anterior" portion of the prosthesis can also become the "posterior" portion of the prosthesis and visa versa.

Further used herein, is the term "press-fit", which is defined as a mechanical engagement formed by two components, at least one of which is deformable, where the adjacent boundary lines of the two components overlap and interface with each other such that the two components must be forced into a position adjacent each other which produces a locking force developed over the area of contact between the two components.

Figure 1:
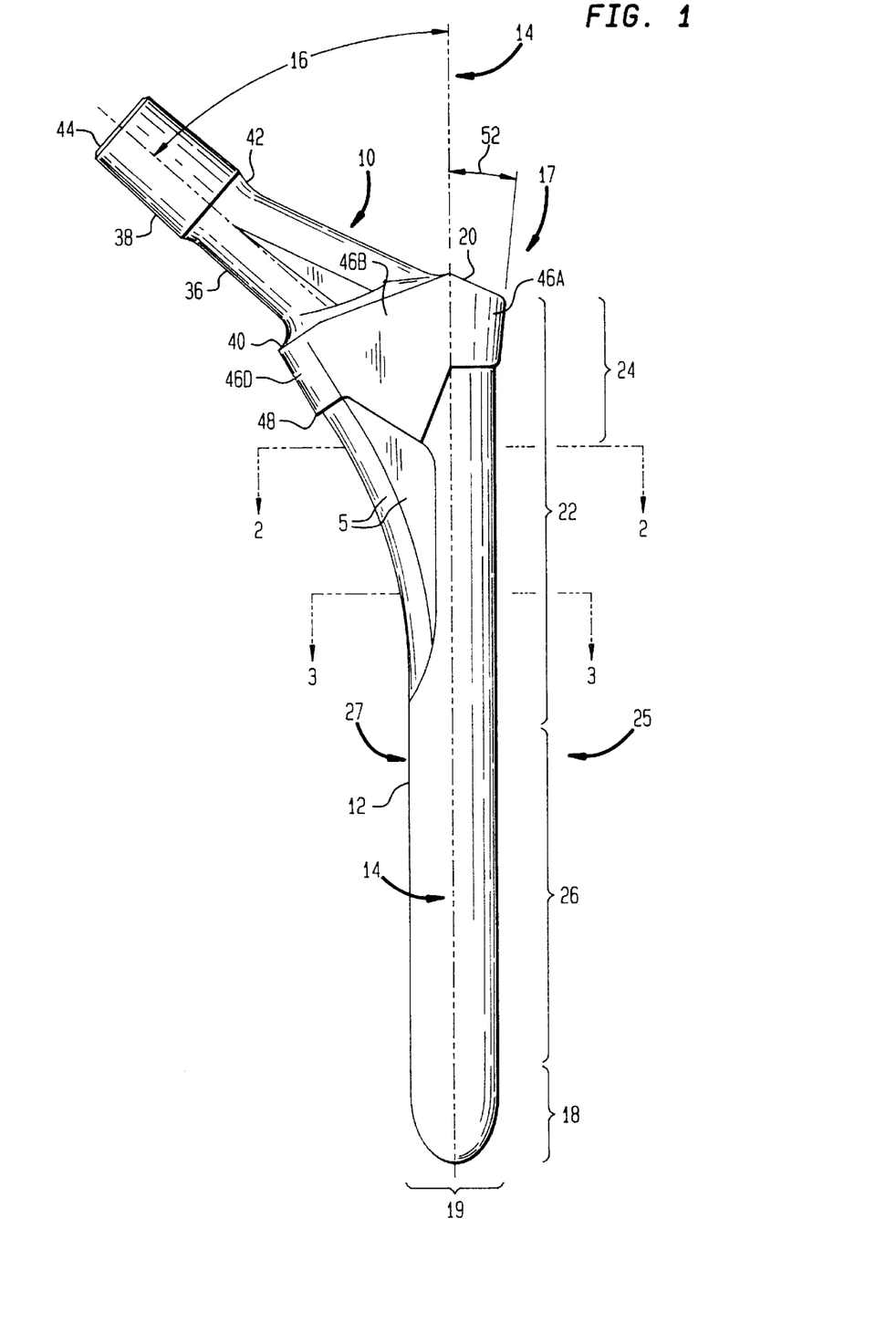
FIG. 1 is an anterior elevational view of the hip implant prosthesis of the present invention.

Referring to FIG. 1, there is shown a side elevational view of a prothesis according to the present invention designated by the numeral 10. The prothesis of FIG. 1 is designed as a femoral component of a hip prosthesis. It is understood, however, that the prothesis according to the present invention can be configured into any other type of implantable prosthetic device. For example, the prosthesis of the present invention can be configured as a humeral component of a shoulder prosthesis. In any event, the prosthesis shown in FIG. 1 is configured as the femoral component of a hip prosthesis and is dimensioned to be press-fitted within a bore formed in the femoral intramedullary canal. The prothesis generally includes a stem 12 having a proximal end 16 and a distal end 18, and a neck 36. The prosthesis 10 further includes a lateral side 25 and a medial side 27. The stem 12 defines a longitudinal axis 14 wherein the neck 36 extends medially, at approximately an angle 16 relative to the longitudinal axis 14, from the proximal end 17 of the stem 12.

A spherically shaped driver recess 20 is formed in the proximal end 16 of stem 12. The driver recess 20 provides an area for the placement of an impaction tool (not shown) which is used to drive the prosthesis into the bore formed in the canal of the femur.

Starting at the proximal end 16 and extending distally therefrom is a tapered portion 22 which defines a proximal locking zone 24 and a recessed medial pocket 50, both of which will be discussed in greater detail below. The tapered portion 22 extends distally from the proximal locking zone 24, merging into a cylindrical portion 26. The free end of the cylindrical portion 26 forms the distal end 18 of the stem 12. The distal end 18 of the stem 12 tapers down from the cylindrical portion 26 to a generally spherical tip portion 19.

Figure 2:
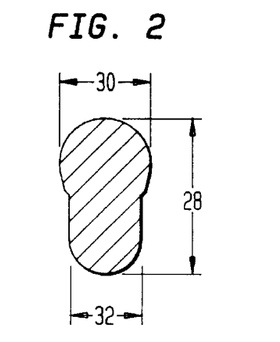
FIG. 2 is a cross-sectional view taken along line 2—2 of FIG. 1.
Figure 3:
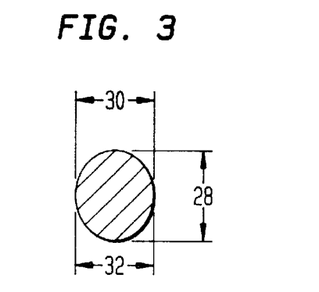
FIG. 3 is a cross-sectional view taken along line 3—3 of FIG. 1.

FIGS. 2 and 3 illustrate the changing cross-sectional shape of the tapered portion 22 at respective lines 2—2 and 3—3. The cross-sectional shape of the tapered portion 22 of stem 12 at line 2—2 (FIG. 2), presents a greater medial-lateral dimension 28 as compared with the overall anterior-posterior dimension 30 (as measured on the lateral side). The cross-sectional shape of the tapered portion 22 changes significantly such that the medial-lateral dimension 28 and anterior-posterior dimension 30 defines an almost circular cross-section at line 3—3, (FIG. 3) approaching the distal end of the tapered portion 22. Also, the anterior-posterior width 30 adjacent the lateral side of the tapered portion 22 becomes substantially greater in width, moving proximally, than the corresponding anterior-posterior width 32 adjacent the medial side.

Referring again to FIG. 1, the neck 36 of the prosthesis 10 is tapered and includes a peg portion 38. The proximal end of the stem 12 merges into the distal end of neck 36 forming a first circumferential fillet at 40. The neck 36 converges proximally as it merges into the tapered portion 38 forming a second circumferential fillet at 42. The tapered portion 38 is slightly tapered in the distal to proximal direction and includes a chamfer 44 at the proximal end of the tapered portion 38. The tapered portion 38 is adapted to receive the femoral bearing head portion of the prosthesis (not shown).

Still referring to FIG. 1, there is illustrated the proximal locking zone 24 portion of the stem 12. The proximal locking zone 24 is comprised of four proximal locking surfaces 46A, 46B, 46C, and 46D which extend circumferentially about the proximal portion of the tapered portion 22 of stem 12. Proximal locking surfaces 46A. 46B, 46C and 46D step down at circumferential step 48 to meet the remaining portion of tapered portion 22.

Figure 4:
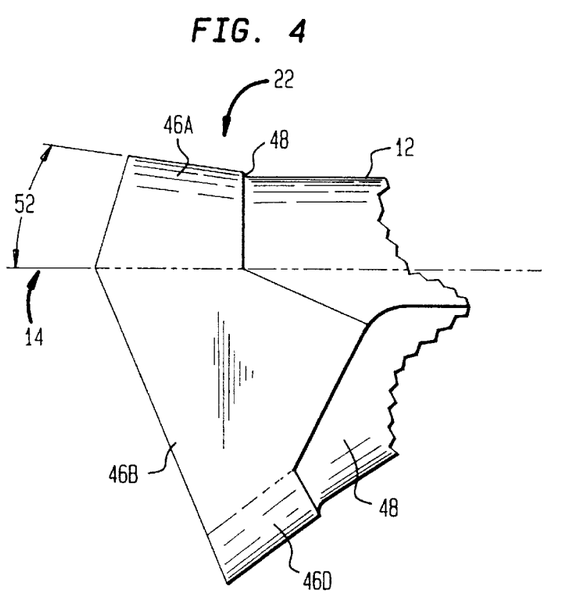
FIG. 4 is a magnified anterior elevational view of the proximal locking zone.

The details of the proximal locking zone 24 are best illustrated by referring to FIG. 4. Locking surface 46A extends between locking surfaces 46B and 46C (not visible) and presents a conically shaped surface on the lateral side of the prosthesis. Locking surface 46D extends between locking surfaces 46B and 46C and presents a curved surface on the medial side of the prosthesis. Locking surfaces 46B and 46C are planar and are located respectively on the anterior and posterior sides of the prosthesis.

Figure 5:
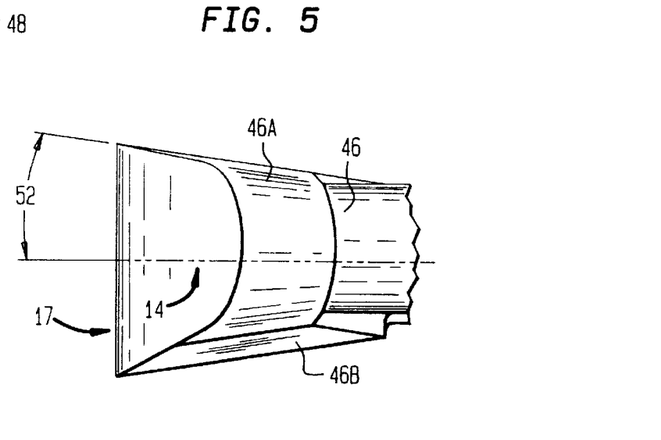
FIG. 5 is a magnified lateral elevational view of the proximal locking zone.

The anteriorly and posteriorly located locking surfaces 46B and 46C each lie in a plane that defines a locking angle 52 which ranges between 5 and 10 degrees and preferably 7 degrees relative to longitudinal axis 14. (see also FIG. 5). Angle 52 is best illustrated in FIG. 5 where the prosthesis has been rotated 4.3° about the longitudinal axis 14.

Referring again to FIG. 4, the conically shaped surface presented by the laterally located locking surface 46A tapers at the same locking angle 52 as locking surfaces 46B and 46C, i.e., between 5 and 10 degrees and preferably 7 degrees relative to longitudinal axis 14 as stated above. The curved surface presented by the medially located locking surface 46D follows the general taper of the medial portion 22 of the stem segment and presents a slightly round surface. This configuration provides an uninterrupted continuum of locking surfaces 46B and 46C.

Figure 6:
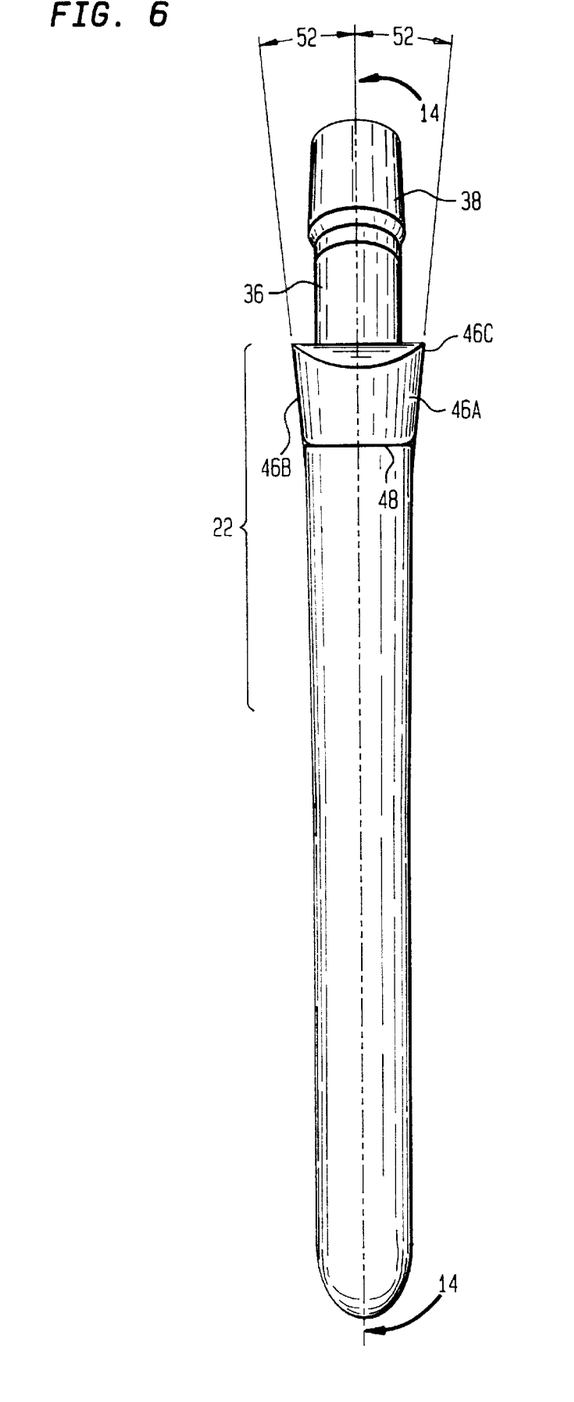
FIG. 6 is a lateral elevational view of the hip implant prosthesis of the present invention.

Referring now to FIG. 6, there is shove the lateral side of the prothesis of the present invention. FIG. 6 clearly illustrates the angle defined by proximal locking surfaces 46B and 46C and the anterior-posterior tapering of the remaining portion of the tapered portion 22.

The prosthesis shown in FIGS. 1–6 is intended to be implanted by a press-fit engagement which does not utilize a cement for locking into place. As such, a layer(s) of bio-active material or "synthetic bone" material is deposited on the proximal locking surfaces 46A, 46B, 46C, and 46D which allow the prosthesis to become permanently attached via a mechanism which includes growth of the natural bone tissue within the cortex of the bone into the layer(s) of bio-active material. The synthetic bone material is generally plasma-sprayed on the prothesis. The preferred choice of synthetic bone material can be any well known ceramic comprising at least one artificial apatite in the form of hydroxyapatite ($Ca50H(P04)2$). This material can be applied in multiple layers and the layers themselves can be composed of different materials. The layer of synthetic bone is designed to be highly compatible with natural bone tissue.

Figure 7:
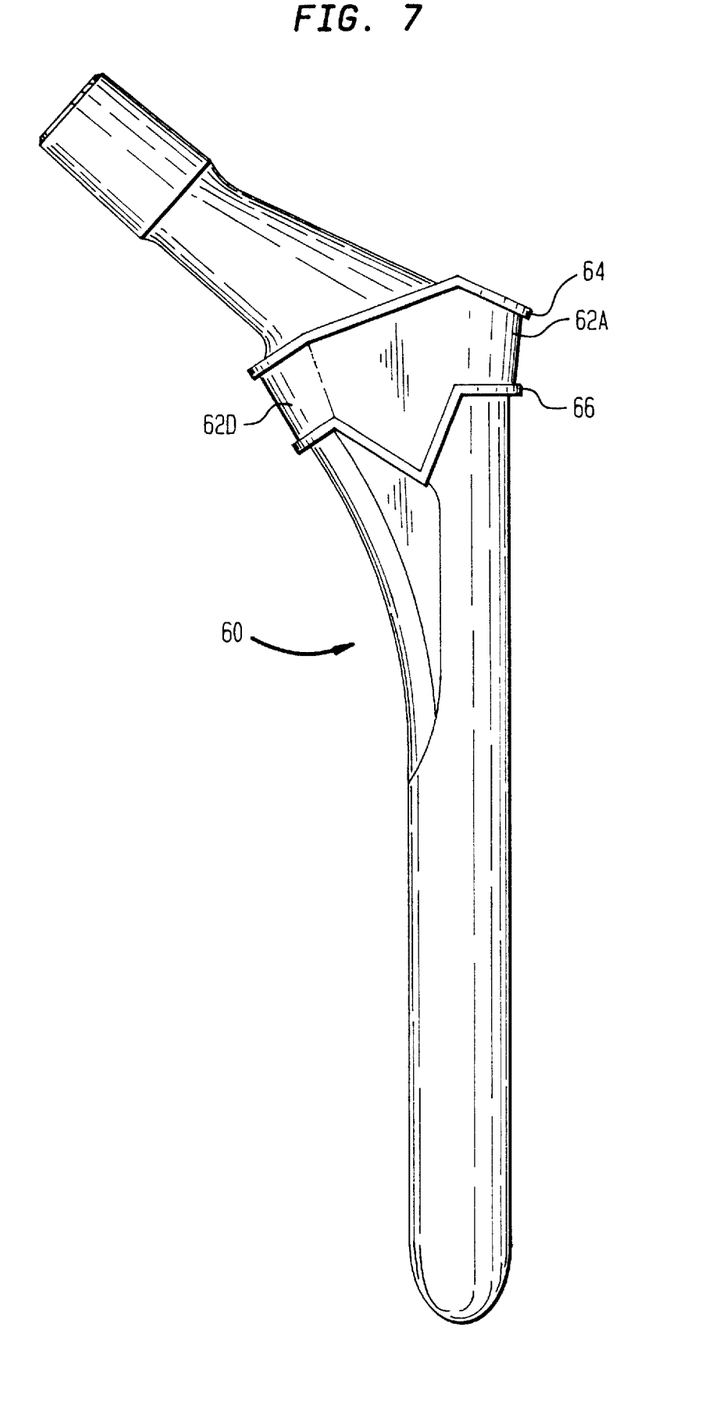
FIG. 7 is an anterior elevational view of an alternative embodiment of the present invention without a plurality of beads.
Figure 8:
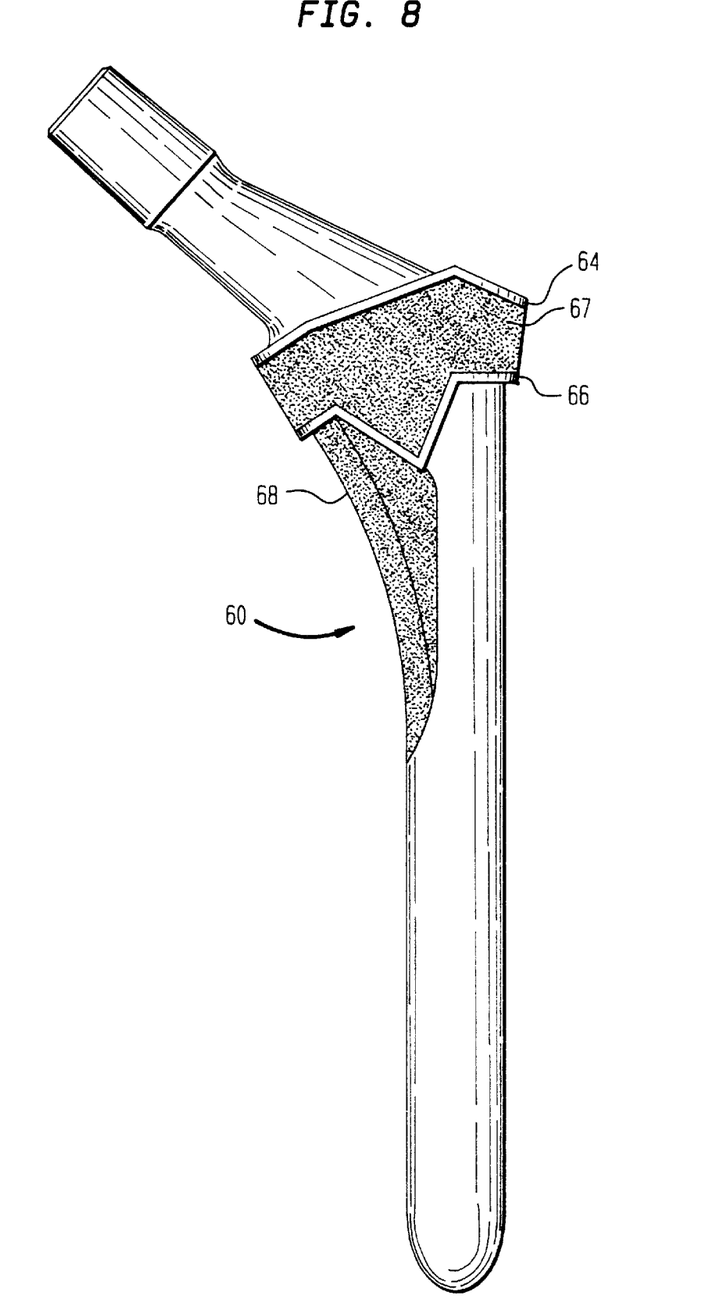
FIG. 8 is an anterior elevational view of the embodiment shown in FIG. 7 with a plurality of beads attached to the proximal locking surface.

Referring now to FIG. 7 there is shown an alternative embodiment of the present invention designated by the numeral 60. The embodiment of FIG. 7 is substantially identical to the embodiment of FIGS. 1–6 except that proximal locking surfaces 62A, 62B, 62C (not visible), and 62D are recessed and bounded by a circumferentially extending proximal ridge 64 and a circumferentially extending distal ridge 66. The proximal locking surfaces are recessed to receive a plurality of beads 67 which act like a porous coating for receiving the ingrowth of the natural bone tissue. The beads can be made from any suitable material such as cobalt chromium or the like. The beads are bonded to the proximal locking surfaces 62A, 62B, 62C, and 62D by sintering as shown in FIG. 8. Note that the medial pocket 50 can also receive a coating of beads if desired, as shown at 68 in FIG. 8, in order to further provide for the ingrowth of natural bone tissue.

The prosthesis of the present invention can be manufactured from titanium alloy, cobalt-chromium alloy or any other suitable material well known in the art. The prosthesis can be made by forging, casting and/or machining operations or any other well known technique.

Referring now to FIGS. 9–19, the apparatus employed in the method of implanting the prosthesis of the present invention is illustrated. Each tool of the apparatus will be explained in connection with the description of the method in which the apparatus is used, which follows.

Figure 9:
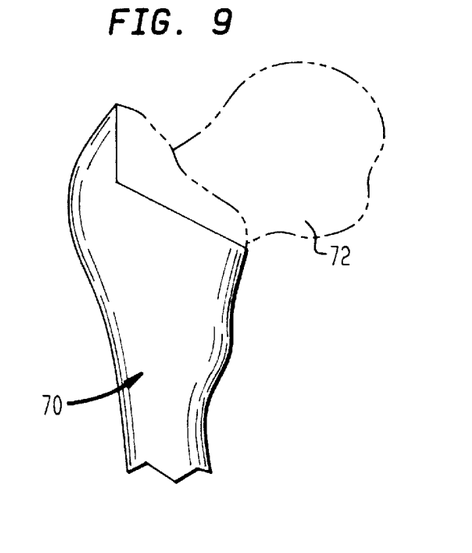
FIG. 9 is a fragmentary view of the proximal end of a femur showing the neck and head thereof in dashed lines, representing the portion of the femur resected in order to implant the prosthesis of the present invention.

Starting with FIG. 9, the proximal end of the femur 70 is presented and the femoral neck 72 is removed using a femoral template (not shown) for determining the area to resect.

Figure 10:
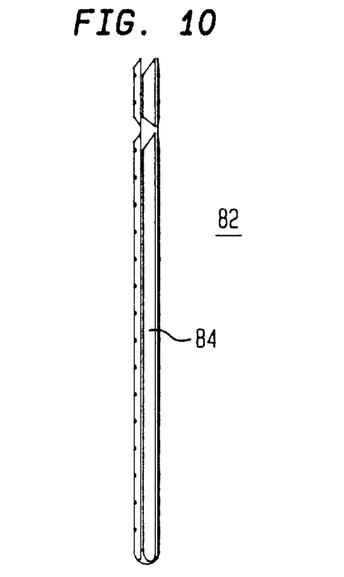
FIG. 10 is an elevational view of the cylindrical reamer.
Figure 11:
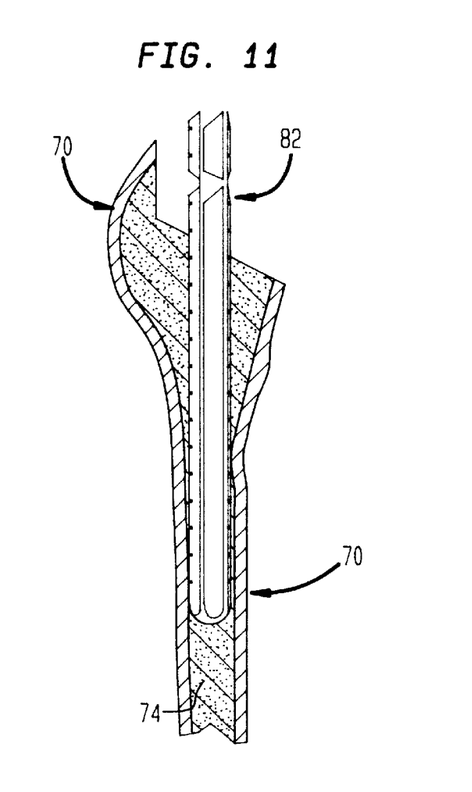
FIG. 11 is a fragmentary cross-sectional view of the proximal end of the femur illustrating the cylindrical reaming tool of FIG. 10.
Figure 12:
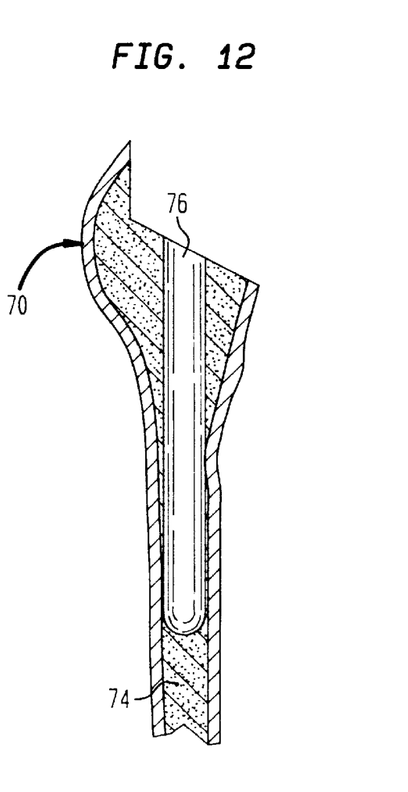
FIG. 12 is a cross-sectional view similar to that of FIG. 11 showing the bore in the medullary canal following the reaming with the cylindrical reamer.

A first cylindrical reamer 82 having straight flutes 84 as shown in FIG. 10. The first cylindrical reamer 82 is inserted in the postero-lateral portion of the resected surface of the femoral neck 72 and enters the medullary canal 74 to form a bore 76 as shown in FIGS. 11 and 12. The cutting flutes 84 of the first cylindrical reamer 82 align the reamer within the medullary canal 74. Successively greater diameter reamers may be used until the desired diameter bore is achieved which is intended to create a line to line fit with the implant stem.

Figure 13:
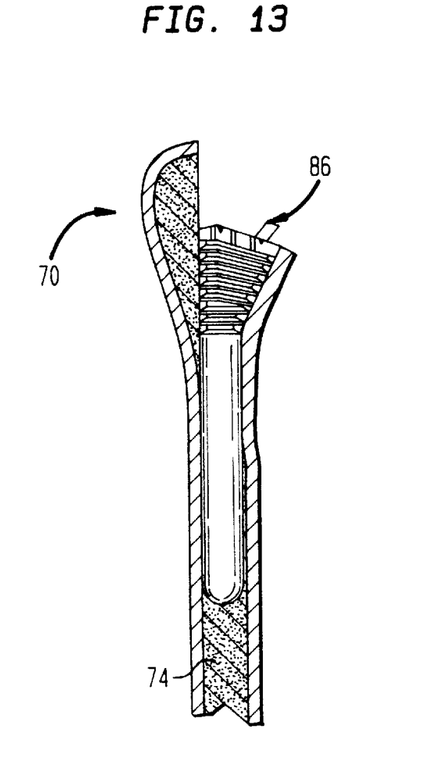
FIG. 13 is a cross-sectional view similar to FIG. 11 but illustrating the use of a rasp to set the initial geometry of the bore for the prosthesis.
Figure 14:
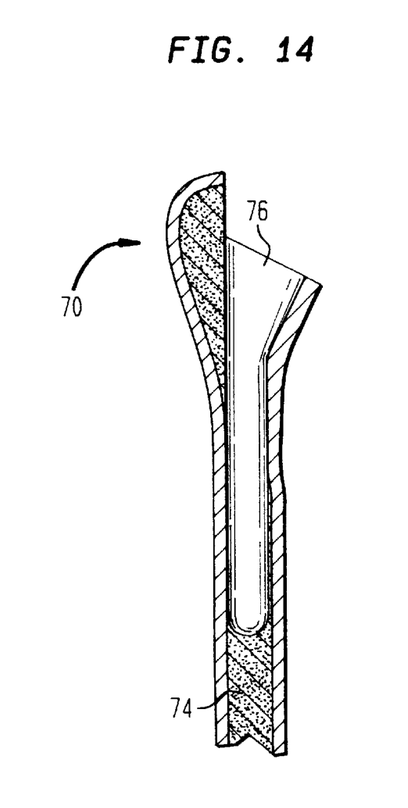
FIG. 14 is a cross-sectional view similar to FIG. 12 but illustrating the geometry of the bore in the medullary canal following the step of reaming with the rasp.
Figure 15:
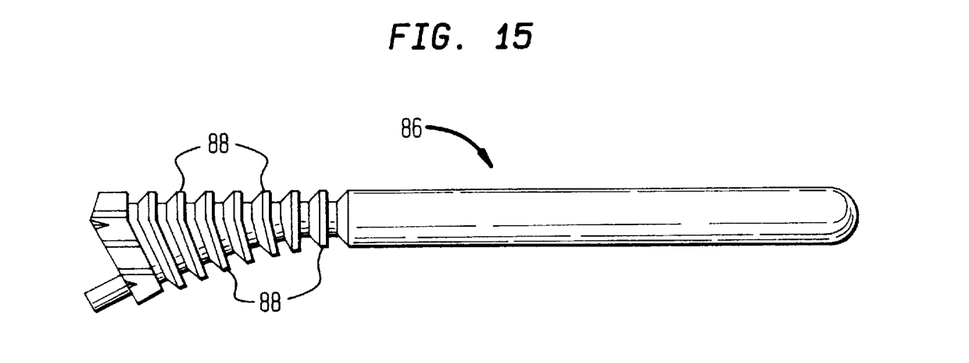
FIG. 15 is an elevational view of the rasp shown in FIG. 13.

Proximal shaping of the bore 76 for the geometry of the stem of the prosthesis is implemented as shown in FIGS. 13 and 14 using a tapered rasp 86 having circumferential cutting teeth 88. As best shown in FIG. 15, the tapered rasp 86 has a profile which is substantially like that of the prosthesis but without the flare characterized by proximal locking surfaces 46A, 46B, and 46C of prosthesis 10. The tapered rasp 86 is inserted and driven into bore 76 as shown in FIG. 13.

Figure 16:
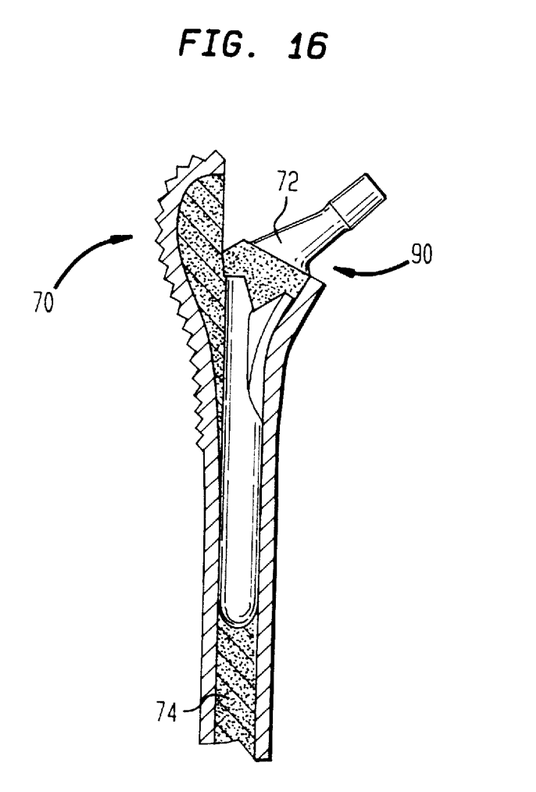
FIG. 16 is a cross-sectional view similar to FIG. 13 but illustrating the use of a trial implant to set the final geometry of the bore for the prosthesis.
Figure 17:
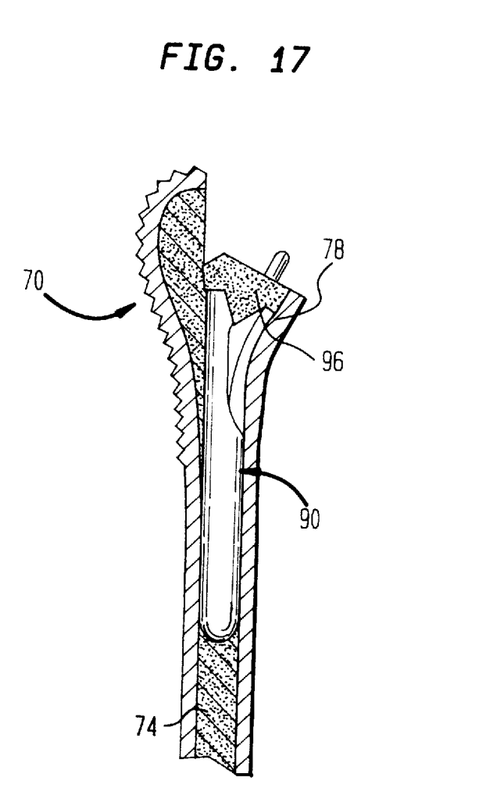
FIG. 17 is a cross-sectional view similar to FIG. 14 but illustrating the final geometry of the bore in the medullary canal following the step of inserting the trial implant.
Figure 18:
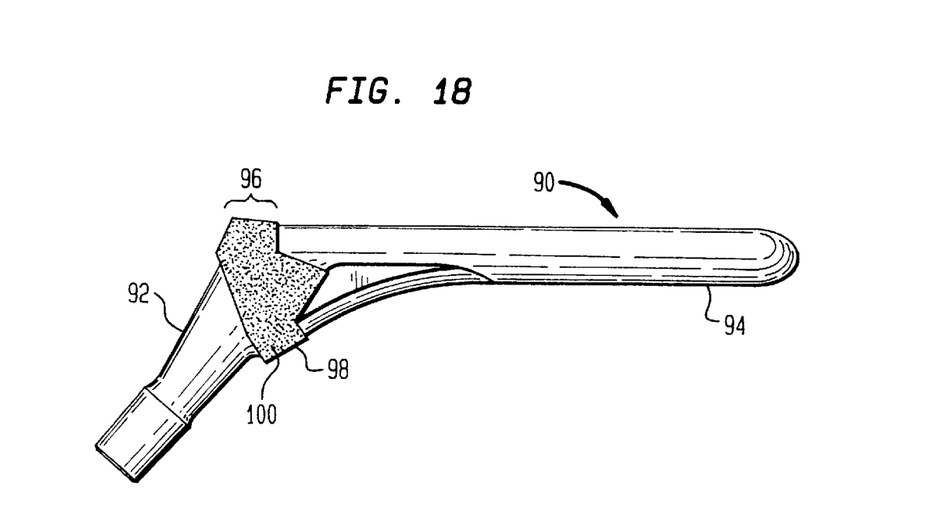
FIG. 18 is an elevational view of the trial stem implant and trial neck implant shown in FIG. 16.

Once the tapered rasp 86 is removed, the final geometry of the bore 76 is formed using a trial implant 90 as illustrated in FIG. 18. The neck 92 and stem 94 of the trial stem implant 90, which are manufactured as separate components, each have a shape and profile which is substantially identical to that of the prosthesis. The trial stem implant 90 includes a proximal locking zone 96 which includes a proximal locking surface 98 with a knurled finish 100 which is designed to prepare the proximal region 78 of the bore 76 for the proximal locking surface of the prosthesis. The trial implant 90 is inserted and driven into the bore 76 as shown in FIG. 16. The illustration of FIG. 17 shows how the proximal locking surface 96 of the trial implant crushes the bone in the proximal region 78 of bore 76 and provides a slightly undersized dimension relative to the prosthesis. This results in a press-fit engagement between the prosthesis and the bore 76 when the prosthesis is driven into the medullary canal 74.

Figure 19:
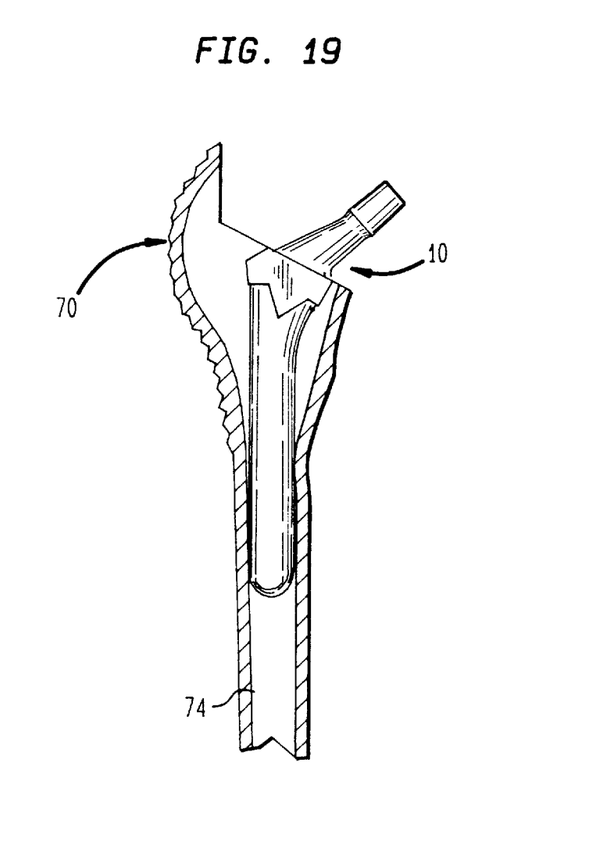
FIG. 19 is a cross-sectional view illustrating the prosthesis implanted into the bore formed in the medullary canal of the femur.

After the trial implant 90 has been removed from the bore 76, the prosthesis 10 is ready to be implanted. As illustrated in FIG. 19, the prosthesis 10 is inserted into the bore 76 and driven into the bore 76 using an impaction tool (not shown) the end of which is placed into the driver recess 20. The prosthesis 10 is driven into the bore 76 until the proximal locking surface is firmly engaged with the proximal region 78. The improved proximal locking zone of the present invention initially loads the proximal-most portion of the bone and greatly compresses the bone thereat. This provides for densification of bone about the stem, greater resistance to subsidence, and greater resistance to torsional forces. In addition, the densification of bone potentially inhibits the transfer mechanism for implant debris to the boundary surrounding the more distal implant/bone interface. A reduction in the incidence of lysis is also a potential benefit.

While it is presently contemplated that the present invention is a hip prothesis, as described herein, the present invention is not limited to uses as a hip prothesis and consequently, may be used as a prosthetic implant of any type. Further, while the present invention is particularly well suited for press-fit implantation, the present invention is not limited to such, and therefore, embodies implantation in any suitable manner. Further, other methods of creating a porous surface on the prosthesis for providing bone ingrowth may be employed and can include porous fiber metal structures such as metal meshes or porous pads which are wrapped around the prosthesis. These and other such methods are contemplated in the present invention for the purpose of enhancing the fixation of the prosthesis within the femur. Any variations or modifications to the invention described herein are intended to be included within the scope of the invention as defined by the appended claims.

We claim:

1. A method for implanting a prothesis stem having a proximal and a distal end into a medullary canal of a femur, said prothesis stem having a proximal locking zone substantially adjacent said proximal end which presents a geometric profile for press-fit engagement within said canal, said method comprising the steps of:

a) resecting a head and neck portion of said femur;

b) reaming a bore along said medullary canal of said femur;

c) inserting a trial implant into said bore to prepare said bore for said geometric profile of said proximal locking zone of said stem, wherein said proximal locking zone of said stem is substantially adjacent said proximal end of said stem and having a geometric profile substantially similar to and of a size less than said geometric profile of said prosthesis stem, wherein said proximal locking zone includes an outwardly flared circumferential proximal locking surface which extends about said proximal end of said stem, said proximal locking surface circumferentially press-fits within the canal of the femur, wherein said outwardly flared circumferential proximal locking surface includes a first planar locking surface on an anterior side of said prosthesis, a second planar locking surface on a posterior side of said prosthesis, and a convex locking surface extending between and merging into said first and second planar locking surfaces on a lateral side of said prosthesis;

d) removing said trial implant from said bore; and e) inserting said prosthesis stem into said bore, said proximal locking zone of said prosthesis stem engaging said bore in a press-fit engagement to securely lock said prosthesis stem into said bore in said medullary canal of said femur.

2. The method according to claim 1, wherein said step of reaming includes a first reaming with a first cylindrical reamer of a given diameter.

3. The method according to claim 2, wherein said step of reaming further includes a second reaming with a tapered reamer after said first reaming, to prepare said bore for said geometric profile of said prosthesis stem.

4. The method according to claim 2, wherein said step of reaming includes a second reaming with a second cylindrical reamer having a diameter substantially greater than said diameter of said first cylindrical reamer.

5. The method according to claim 4, wherein said step of reaming further includes a third reaming with a tapered reamer after said second reaming, to prepare said bore for said geometric profile of said prosthesis stem, and wherein said trial implant includes a proximal locking zone which presents a geometric profile substantially like said geometric profile of said locking zone of said stem, said geometric profile of said trial implant being of a size which is slightly less than a size of said geometric profile of said stem.

6. The method according to claim 1 wherein said proximal locking surfaces of said trial implant are recessed and bounded by a circumferentially extending proximal ridge and a circumferentially extending distal ridge.

* * * * *